United States Patent [19]

Mykleby

[11] Patent Number: 4,660,721
[45] Date of Patent: Apr. 28, 1987

[54] STERILIZATION PACKAGE

[75] Inventor: Laurie G. Mykleby, Palos Park, Ill.

[73] Assignee: CVP Systems, Inc., Downers Grove, Ill.

[21] Appl. No.: 848,570

[22] Filed: Apr. 7, 1986

[51] Int. Cl.⁴ .................. B65D 65/40; B65D 81/20
[52] U.S. Cl. .................. 206/439; 206/438; 206/484.1; 206/484.2
[58] Field of Search ........... 206/438, 439, 484, 484.1, 206/484.2, 363

[56] References Cited

U.S. PATENT DOCUMENTS

| | | | |
|---|---|---|---|
| 3,073,507 | 1/1963 | Trewella et al. | 206/439 |
| 3,419,136 | 12/1968 | Pratt | 206/438 |
| 3,685,720 | 8/1972 | Brady | 206/484 |
| 3,768,725 | 10/1973 | Pilaro | 206/439 |
| 4,055,672 | 10/1977 | Hirsch et al. | 206/439 |
| 4,057,144 | 11/1977 | Schuster | 206/439 |
| 4,203,520 | 5/1980 | Schuster | 206/439 |
| 4,367,816 | 1/1983 | Wilkes | 206/439 |

Primary Examiner—Stephen P. Garbe
Assistant Examiner—Brenda J. Ehrhardt
Attorney, Agent, or Firm—Thomas W. Speckman

[57] ABSTRACT

Multi-layer sterilization package and process for sterilizing equipment wherein items are placed in the multi-layer sterilization package which is adapted for use with a snorkel-type gas treatment apparatus; substantially all gas is withdrawn from the interior of the package; sterilization gas is injected into the interior and retained for a time sufficient to sterilize the equipment; sterilization gas is withdrawn from the package; and a cushioning gas is introduced into the package. The package is sealed to retain the cushioning gas, providing for effective gas leak detection.

8 Claims, 6 Drawing Figures

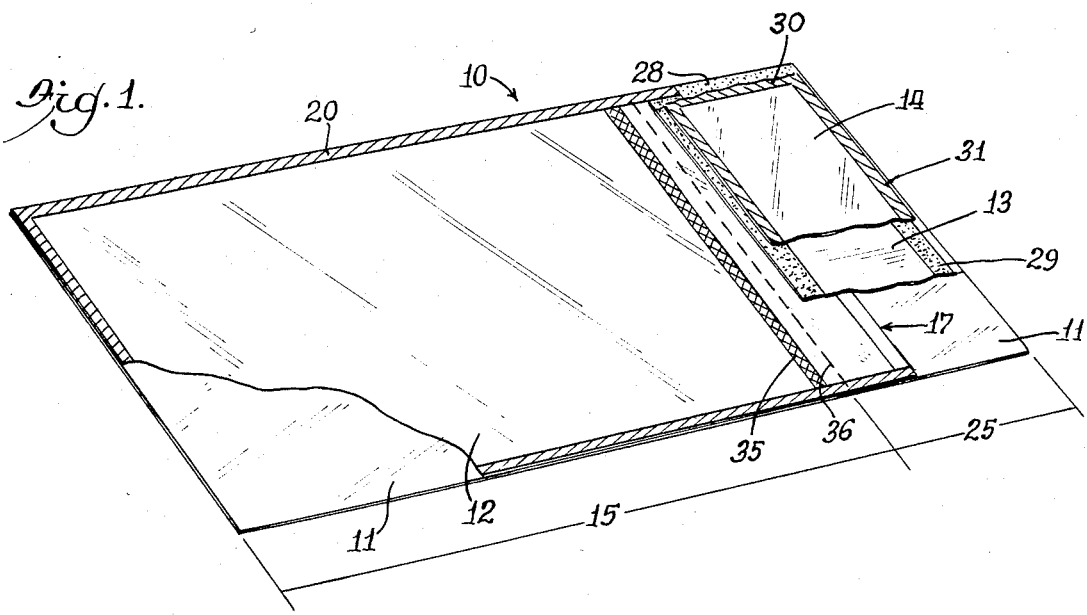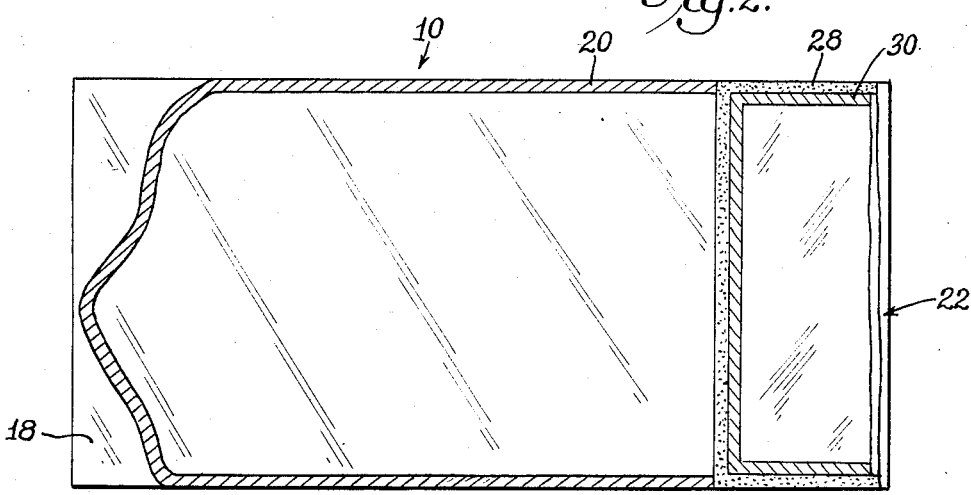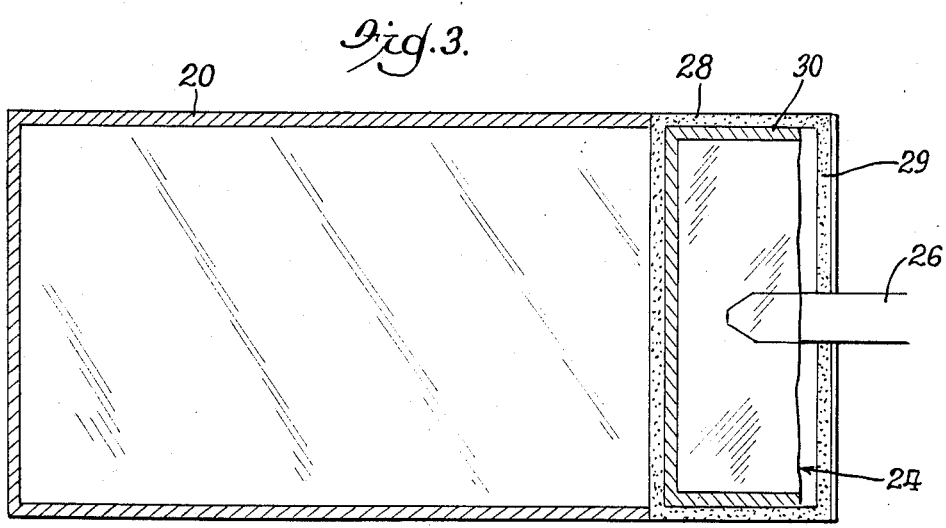

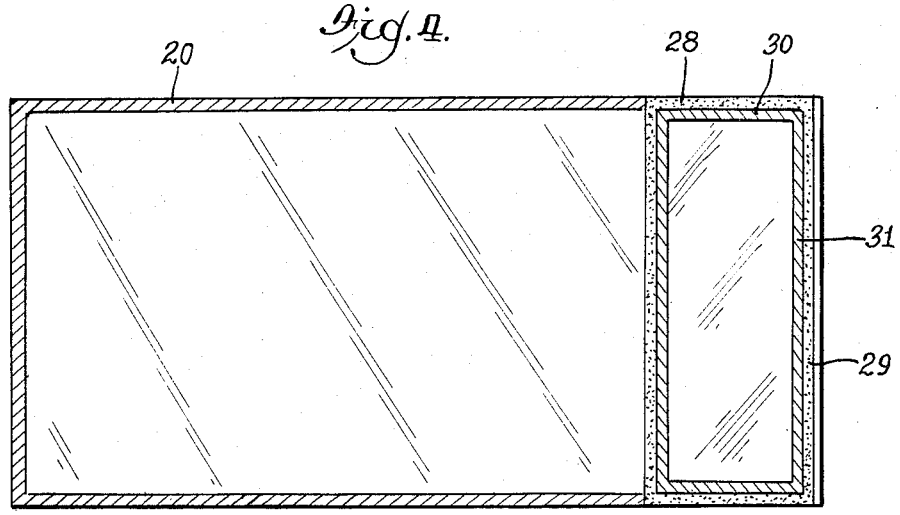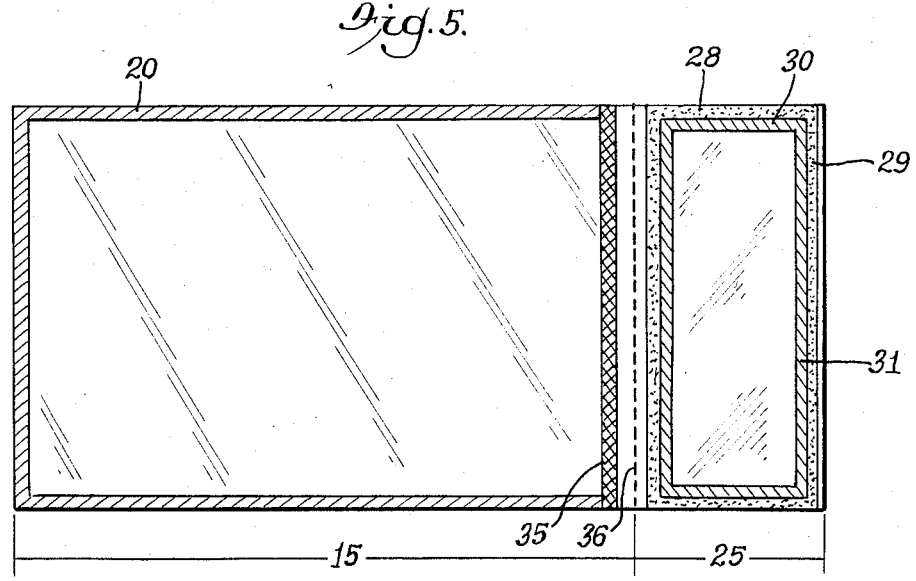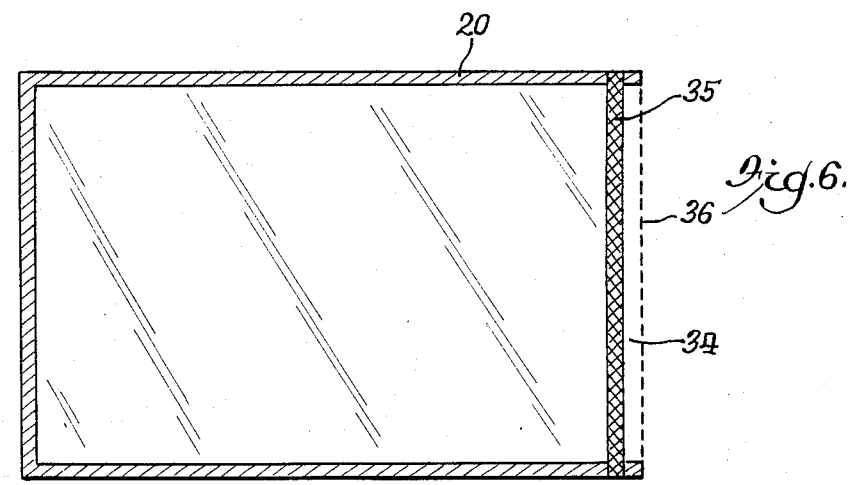

4,660,721

STERILIZATION PACKAGE

BACKGROUND OF THE INVENTION

1. Field of the Invention

This invention relates to an improved, multi-layer sterilization package and a simplified process for sterilizing equipment, particularly medical appliances and supplies.

2. Description of the Prior Art

It is highly desirable to sterilize many different types of medical appliances and supplies to eliminate contamination in the form of living microorganisms and/or macroorganisms prior to utilization of the appliances or supplies in medical, research, testing or other applications. It is essential to sterilize any equipment or substance which is introduced into an organism to prevent infection and contamination of the organism. Hospitals and research institutions thus require large quantities of sterile appliances and supplies in stock at all times. It is important that the sterile appliances and supplies retain sterility, and are packaged in a convenient form which is easily stored and which provides convenient access to the sterile contents.

Institutions which require and use sterile appliances and supplies in a large volume have essentially two choices. Prepackaged, disposable, sterile appliances and supplies may be purchased from vendors. The primary disadvantages of prepackaged, disposable, sterile appliances and supplies are that they are very costly, and that many precision instruments cannot be provided in a cost effective, disposable form. The alternative to purchasing packaged, disposable, sterile equipment and supplies is to sterilize reusable equipment and supplies and after use, clean and sterilize equipment and supplies to ready them for subsequent use. This process is costly because it is very labor intensive.

Several procedures for sterilizing appliances and supplies are available. One of the commonly used techniques is autoclaving, wherein objects to be sterilized are subjected to elevated temperatures and pressures to exterminate any living organisms. Items are ordinarily autoclaved in a large chamber which is equipped with elaborate temperature and pressure control and containment mechanisms. Objects to be autoclaved must be prepared for autoclaving; they must be clean and dry, and they must be wrapped or covered to at least some extent. Some applications require that an item be sterilized in its entirety, while other applications require only that interior surfaces or portions remain sterile. Items must be carefully prepared prior to autoclaving treatment to permit elevated temperature and pressure to penetrate to the interior of the container or the packaging, and yet to provide a barrier to prevent contamination from entering the packaging after autoclaving treatment. This process is extremely labor intensive, and it is also highly unreliable.

Another sterilization technique known to the art involves the use of a sterilization gas. Equipment or supplies to be sterilized may be sealed in a packaging device having a gas permeable membrane. Gases present in the sealed packaging device are evacuated through the gas permeable membrane, and sterilization gas is injected into the package, again through the gas permeable membrane. The sterilization gas, after a suitable sterilization time period, may be withdrawn, if desired. Gas evacuation and injection of many individual packages may take place simultaneously in a large sealed chamber, which requires elaborate pressure regulation and containment equipment.

Equipment may also be sterilized by direct exposure to ultraviolet radiation. Sterilization procedures utilizing ultraviolet radiation require extensive protective measures since ultraviolet radiation may cause very serious, permanent damage to living cells.

SUMMARY OF THE INVENTION

The improved sterilization package and process of this invention permits sterilization of individual packages of appliances and supplies using a simplified and highly reliable technique. The sterilization package comprises a multi-layer package which is adapted to be used with a snorkel-type gas evacuation and/or gas injection apparatus, or the like, which achieves gas evacuation and gas injection of individual packages. The improved sterilization package and sterilization process of this invention is cost effective and, most importantly, it is highly reliable, since the sterilization conditions can be set and monitored for each individual sterilization package. The sterilization process of this invention also provides a simple and effective gas leak detection means whereby gas leaks from individual sterilized packages are detectable to indicate that sterile conditions no longer exist.

The sterilization package and process of this invention may be utilized in connection with disposable equipment which is designed to be sterilized, used and discarded, or with reusable equipment which is thoroughly cleaned and dried after each use and prior to each sterilization procedure. The configuration and dimensions of the sterilization package may conform to any desired or required configuration to permit packaging and sterilization of very small or very large pieces of equipment or instruments, and to permit packaging and sterilization of individual instruments, pieces of equipment, or supplies, or to permit sterilization of an assembly comprising several elements, or to permit packaging and sterilization of multiple instruments or pieces of equipment in a single pouch.

The multi-layer sterilization package of this invention comprises first and second flexible, sealable, gas impermeable layers, the second layer being smaller than the first layer; a third flexible, sealable, gas permeable, but organism impervious layer attached to the second layer, the second and third layers together being about the size of the first layer; and a fourth flexible, sealable, gas impermeable layer about the same size as and attached over the third layer. The first and second flexible, gas impermeable, sealable layers comprise the major portion, or body of the sterilization package. These layers may comprise a metallic foil, such as aluminum foil, laminated on one side or coextruded with a sealable material, preferably a heat sealable material, which enables the two layers to be hermetically sealed to one another. These layers may also comprise a paper or synthetic material or laminate which is sealable and gas impermeable. The first, lower layer extend for the full length of the packaging device, while the second, upper layer extends throughout the body portion of the packaging device, for a substantial portion of the first layer, preferably about 50 to 95 percent of the entire length of the sterilization package.

The first and second layers may comprise two separate sheets of flexible, gas impermeable, sealable material which are sealed along at least two sides to form a pouch with an opening through which instruments, equipment or supplies to be sterilized may be passed to the interior of the pouch and an opening to the operations portion as more fully described below. In a preferred embodiment, the first and second layers are sealed together along three sides leaving one side open to the operations portion and objects are passed into the interior through the same opening. The first and second layers of the packaging device may alternatively comprise a single long piece of flexible, gas impermeable, sealable sheet material which is folded over on itself at one end to form two layers, the second, upper layer shorter than the first, lower layer, and hermetically sealed along at least one side. In a preferred embodiment, two generally rectangular layers are sealed along three sides to form an enclosed interior having generally rectangular dimensions, and accessible from the outside through the unsealed side.

The sterilization package of this invention is not necessarily rectangular. The first and second layers are preferably similar in configuration, but may be of any configuration which is convenient to sterilize equipment, supplies, instruments, etc. First and second layers having a polygonal or rounded configuration may be sealed to form a pouch having an enclosed interior space of the desired configuration. It is only important that first and second flexible, gas impermeable, sealable layers are sealed along a substantial portion of their perimeter, leaving an opening through which instruments and equipment may be inserted into the interior of the pouch, and that the first, lower layer extends beyond the second, upper layer at an area which is open.

A third flexible, gas permeable but microorganism impervious, sealable layer has dimensions which correspond approximately to the dimensions of the portion of the first layer which extends beyond the unsealed end of the second layer. The third layer is sealed to the surface of the second layer along the entire length of its unsealed end, and sealed to the sides of the first layer which extend beyond the unsealed end of the second layer. In a preferred embodiment, the third layer is not sealed along the end which is adjacent the unsealed end of the first layer to retain an opening through which items to be sterilized may be inserted into the pouch. The second layer and the third gas permeable layer, sealed to each other, form a continuous part which corresponds, approximately, to the dimensions of the first layer.

A fourth layer having approximately the same dimensions as the third layer comprises a flexible, gas impermeable, sealable sheet material. The fourth layer is hermetically sealed to the third layer on three sides leaving an opening between the third and fourth layers along one side. In a preferred embodiment, all four layers are left unsealed at the same end to permit ready access to the interior of the body portion of the pouch and to form an interior space between the third and fourth layers.

The sterilization package comprises a body portion defined by the first and second layers comprising approximately 50 to 95 percent, preferably about 80 to 90 percent of the total length of the sterilization package, described above, and an operations portion defined by the third and fourth layers comprising approximately 5 to 50 percent, preferably about 10 to 20 percent of the total length of the sterilization package.

The advantages of this sterilization package and of the operations space formed between the third and fourth layers will become clear as utilization of the multi-layer sterilization package is described with reference to the improved sterilization process of this invention. Items to be sterilized are placed in the pouch interior in the body portion of the sterilization package through an instrument insertion opening provided at one side of the sterilization package. After the items to be sterilized have been arranged in the pouch interior, the unsealed sides of the first, second and third layers are hermetically sealed to provide a sterilization pouch which is sealed along its outer perimeter. The sterilization package, in this condition, undergoes gas evacuation and sterilization gas injection procedures. All seals formed between all layers must be continuous and must be hermetic. It is understood that any type of continuous hermetic seal may be utilized with the process and apparatus of this invention. Heat sealing is utilized in a preferred embodiment to simply and conveniently provide a reliable hermetic seal.

Individual sterilization pouches are adapted to undergo gas evacuation and gas injection individually by means of a single processing machine having a snorkel-type arrangement for evacuation and injection of gases. Suitable machines are known to the art, and are presently used in the meat and food packaging industries. Suitable processing machines have gas withdrawal and injection means, and may be provided with suitable injection gases. The packaging machine taught by U.S. Pat. 4,241,558, incorporated herein by reference, is suitable for use in the process of this invention. A snorkel apparatus or any other suitable gas evacuation means is positioned in gas tight relation in the operations space between the third, gas permeable layer and the fourth, gas impermeable layer and gas is withdrawn from the pouch interior space by means of a vacuum system of the processing machine. Sterilization gas is then injected into the pouch interior to a suitable pressure. Alternatively, gas evacuation and sterilization gas injection of many sterilization pouches may take place simultaneously in a large, sealed chamber. Suitable sterilization gas composition, pressure and retention time of sterilization gas within the pouch interior are well known to the art, or may be determined upon routine experimentation.

Following a suitable retention time of sterilization gas within the sterilization pouch, sterilization gas is withdrawn from the pouch, preferably using a snorkel-type gas evacuator or similar apparatus. According to one embodiment, gas treatment is complete upon evacuation of sterilization gas from the pouch interior. For the evacuation of sterilization gas, a suitable vacuum may be drawn, and the fourth layer sealed to prevent any transfer of gas into the pouch interior. The first layer is then sealed to the second layer just below the operations portion of the package along a final process seal, and the body portion of the sterilization pouch is severed from the operations portion along a final cut line. The operations portion of the packaging device may be discarded and the sealed body portion of the sterilization pouch containing sterilized equipment is ready for storage or use.

According to another embodiment, after sterilization gas has been evacuated from the pouch interior, an inert and non-reactive gas which serves as a cushioning gas and/or a leak detection gas, may be injected between the third and fourth layers through the gas permeable membrane and into the interior space. The pressure of the cushioning gas may expand the fourth layer to create a bubble formation. The unsealed portion of the fourth layer is then sealed to retain the cushioning and/or leak detection gas. The preserving and/or leak detection gas crosses the gas permeable membrane comprising the third layer, entering the body space of the sterilization package to cushion the sterilized equipment in the pouch interior. With the sterilization and gas treatment procedures thus completed, the first and second layers comprising the body of the pouch are sealed to each other along a final process seal just below the operations portion of the pouch. The operations portion of the pouch may then be removed from the body portion of the pouch and discarded. The sterilized equipment is contained within a gas cushioned pouch which is hermetically sealed around its entire perimeter. Gas cushioning of the sterilized equipment within the pouch is advantageous because it diminishes the incidence of pouch puncture by the instruments within the bag during handling and use, and it provides for reliable leak detection by gas detectors. At least a small portion of the first and second layers preferably extends beyond the final seal to provide for convenient handling and opening of the pouch by peeling the two layers apart from each other along the seals.

BRIEF DESCRIPTION OF THE DRAWINGS

Specific embodiments of the sterilization package of this invention which are suitable for use with the process of this invention are shown in the figures wherein:

FIG. 1 shows a perspective view of a multi-layer sterilization package, partially cut away to illustrate the relationship of the various layers with respect to one another and all of the process seals;

FIG. 2 shows a multi-layer sterilization package ready to receive instruments or equipment to be sterilized;

FIG. 3 shows the sterilization package of this invention in a condition for gas evacuation and injection treatment by a snorkel-type apparatus of a processing machine;

FIG. 4 shows the sterilization package of this invention after cushioning gas has been injected;

FIG. 5 shows the final process seal on the body portion of the sterilization package and the final cut line; and FIG. 6 shows the sterilized pouch comprising the body portion of the sterilization package, with the operations portion of the sterilization package removed.

DESCRIPTION OF PREFERRED EMBODIMENTS

As shown in FIG. 1, the sterilization package of this invention comprises sterilization pouch 10 having a multi-layer construction. Sterilization pouch 10 comprises first layer 11, second layer 12, third layer 13, and fourth layer 14. First layer 11 and second layer 12 preferably comprise a flexible, gas impermeable, heat sealable sheet material, such as a metallic foil, a synthetic sheet material, or a coated paper laminated or coextruded with a heat seal forming material. First layer 11 and second layer 12 are continuously and hermetically heat sealed to one another along a substantial portion of their perimeters. FIG. 1 shows a rectangular sterilization pouch 10, but any other useful configuration for the sterilization pouch may be utilized. Similarly, the dimensions of the sterilization pouch are not important and any suitable dimensions may be utilized for sterilizing different types and sizes of equipment.

As shown in FIG. 1, first layer 11 has a larger surface area than second layer 12. Sterilization pouch 10 comprises two portions: a body portion 15 comprising the portions of first layer 11 and second layer 12 which are continuously sealed up to final cut line 36, and operations portion 25 comprising those elements on the right-hand side of final cut line 36, as shown in FIG. 1, including part of first layer 11, and third and fourth layers 13 and 14 in their entireties. First layer 11 thus extends over both body portion 15 and operations portion 25, while second layer 12 extends for only a short distance into operations portion 25 past final cut line 36. In the embodiment shown in FIG. 1, first layer 11 and second layer 12 comprise two separate sheets which are approximately coextensive in body portion 15, and which are continuously and hermetically heat sealed along the three sides which are coextensive, shown as hermetic heat seal 20, leaving second layer opening 17 extending for the length of the fourth side. Second layer 12 preferably extends for about 50 to 95 percent the length of first layer 11, and more preferably from about 80 to 90 percent the length of first layer 11.

Third layer 13 preferably comprises a flexible, gas permeable but microorganism impervious, heat sealable sheet material. Synthetic sheet materials such as Tyvek, a product sold by DuPont, and the like, are suitable for third layer 13. As shown in FIG. 1, third layer 13 is generally coextensive with operations portion 25 of sterilization pouch 10. In the initial pre-sterilization condition of sterilization pouch 10, third layer 13 is continuously and hermetically heat sealed to layers 11 and 12 along three sides, leaving third layer opening 22 to serve as an instrument insertion opening.

Fourth layer 14 preferably comprises a flexible, gas impermeable, heat sealable sheet material. Sheet materials such as ethyl acrylic acid and synthetic polymeric and plastic materials are suitable for fourth layer 14. Fourth layer 14 is generally coextensive with third layer 13 and is continuously and hermetically heat sealed to third layer 13 or to first layer 11 and second layer 12 along three sides at fourth layer hermetic heat seal 30 which is approximately coextensive with third layer hermetic heat seal 28, as shown in FIG. 2. Fourth layer 14 remains unsealed along fourth layer gas treatment opening 24 to provide access to an operations space formed between the third and fourth layers.

Hermetic heat seals 28 and 30 may be aligned to provide hermetic heat sealing of third layer 13 and fourth layer 14 in the same positions, or hermetic heat seals 28 and 30 may be slightly displaced from one another. Although hermetic heat seals 20, 28 and 30 are shown extending to the edges of the sheet materials comprising first layer 11, second layer 12, third layer 13 and fourth layer 14, it will be understood that hermetic heat seals 20, 28 and 30 may be displaced slightly inwardly from the edges of the sheet materials. As shown in FIG. 2, hermetic seal 20 sealing the edges of first layer 11 and second layer 12 may have any configuration which is convenient for the items being sterilized. If hermetic heat seal 20 does not extend to the edges of first layer 11 and second layer 12, excess unsealed layers 18, shown in FIG. 2, extend from the hermetic seal and need not be trimmed or discarded.

Sterilization pouch 10 in its sterilization-ready form is best illustrated in FIG. 2. Sterilization pouch 10 comprises a flat, lightweight package which may be conveniently and inexpensively stored and transported.

The improved sterilization process of this invention will be described with reference to FIGS. 2-6 which illustrate the process steps sequentially. According to the improved sterilization process of this invention, items to be sterilized are inserted through instrument insertion opening 22 to the pouch body interior of body portion 15 formed between first layer 11 and second layer 12 in the sterilization pouch shown in FIG. 2. After items to be sterilized are placed in the pouch body interior, instrument insertion opening 22 is continuously and hermetically heat sealed at third layer process seal 29, shown in FIG. 3. After third layer process seal 29 is formed, a fully enclosed, hermetically sealed interior space extending throughout body portion 15 and operations portion 25 is provided.

After third layer process seal 29 has been formed, a snorkel-type gas treatment apparatus, shown schematically as 26 in FIG. 3, may be inserted in gas treatment opening 24 formed between fourth layer 14 and third layer 13. Snorkel-type gas treatment apparatus 26 may take any of a variety of forms, and it is important only that it is capable of withdrawing gas from and injecting gas into the interior of body portion 15 through third layer 13 which comprises a gas permeable but microorganism impervious sheet material. Snorkel-type gas treatment apparatus 26, positioned in gas tight relation in gas treatment opening 24, withdraws gases from the interior space of body portion 15 and operations portion 25 by means of vacuum withdrawal. Gas is withdrawn until a suitable vacuum pressure has been attained in the pouch interior. Suitable vacuum pressures are known to the art, or may be determined upon routine experimentation.

After the gas is withdrawn and a vacuum has been established, sterilization gas is injected through the third layer into the interior of body portion 15 and operations portion 25, preferably by means of snorkel-type gas treatment apparatus 26. Suitable sterilization gas and gas mixtures are well known to the art. Sterilization gas is injected in a sufficient quantity to effect sterilization of the contents. Alternatively, gas withdrawal and sterilization gas injection of sterilization pouches may take place in a large, sealed chamber, as is known to the art. Sterilization gas is retained inside sterilization pouch 10 for a sufficient residence time to sterilize the contents and the interior surface of sterilization pouch 10.

After a sufficient sterilization gas residence time has elapsed, sterilization gas is evacuated from sterilization pouch 10 by snorkel-type gas treatment apparatus 26 and a vacuum is again established in the interior of body portion 15 and operations portion 25. Suitable sterilization gas composition, pressure, and retention time of sterilization gas within the pouch interior are well known to the art, or may be determined upon routine experimentation.

According to one embodiment of the process of the present invention, body portion 15 of sterilization pouch 10 is continuously and hermetically heat sealed at final hermetic heat seal 35 as shown in FIG. 5, after evacuation of sterilization gas. Snorkel-type gas treatment apparatus 26 is removed from gas treatment opening 24, and body portion 15 is severed from operations portion 25 along final cut line 36. The hermetically sealed pouch interior of body portion 15 according to this embodiment, is at a negative pressure relative to atmospheric pressure, and the first and second layers thus conform generally to the profile of the sterilized items contained in pouch interior 16.

According to a preferred embodiment of the process of this invention, after sterilization gas is evacuated from the interior of body portion 15 by snorkel-type gas treatment apparatus 26 and a vacuum is established, a cushioning and/or leak detection gas is backflushed into the interior of the pouch by snorkel-type gas treatment apparatus 26. Backflushing gas may comprise any suitable gas or gas mixtures which are non-reactive with the packaging device and its sterilized contents and which are inert with respect to subsequent applications of the sterilized contents. Backflushing gas preferably comprises carbon dioxide and/or nitrogen in admixture with other inert, non-reactive gases. Cushioning and/or leak detection gas is backflushed into the sterilization pouch to achieve a pressure of about atmospheric pressure or less in the pouch interior.

Injection of backflushing gas into sterilization pouch 10 cushions the sterilized items in the pouch interior, thereby diminishing the risk of punctures to the sterilization pouch. In addition, backflushing gas may provide ready detection of leaks in sterilization pouch 10. Individual sterilization pouches may be analyzed by gas detectors to identify pouches in which sterile conditions no longer exist. Backflushing gas is injected through third layer 13 into body 15 of sterilization pouch 10. Fourth layer 14 may be expandable, and the gas pressure may create a bubble formation in fourth layer 14. At this point, snorkel-type gas treatment apparatus 26 may be withdrawn from gas treatment opening 24 and fourth layer process heat seal 31 may be applied. Backflushing gas between third layer 13 and fourth layer 14 is transported through gas permeable microorganism impervious third layer 13 until the gas pressures on both sides of third layer 13 have equilibrated. This equalization of pressures assures that a suitable amount of backflushing gas has been conveyed to the pouch interior. Sterilization pouch 10 is shown at this point in the process at FIG. 4. Sterilization and gas treatment is now complete and a final hermetic heat seal is applied to seal first layer 11 to second layer 12 at final hermetic heat seal 35. Operations portion 25 may now be severed from body portion 15 along final cut line 36, and operations portion 25 may be discarded. Cut line 36 is preferably slightly displaced from final hermetic heat seal 35, thus providing excess unsealed layers 34. Excess unsealed layers 34, comprising first layer 11 and second layer 12, provide gripping edges so that the two layers may be conveniently peeled apart to provide access to the sterilized items in the pouch interior.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein may be varied considerably without departing from the basic principles of the invention.

I claim:
1. A multi-layer sterilization package comprising:
a first flexible, sealable, gas impermeable layer;
a second flexible, sealable, gas impermeable layer smaller than said first layer and hermetically sealed to said first layer along a substantial portion of its perimeter to form an accessible interior space be- tween said first and second layers, one end of said second layer remaining unsealed;

a third flexible, sealable, gas permeable, organism impervious layer hermetically sealed at least to said unsealed end of said second layer to retain said accessible interior space, at least one end of said third layer remaining unsealed;

a fourth flexible, sealable, gas impermeable layer hermetically sealed to and overlaying said third layer, at least one end of said fourth layer remaining unsealed.

2. A multi-layer sterilization package according to claim 1 wherein said unsealed ends of said third and fourth layers retain said interior space accessible and form an operations interior space between said third and fourth layers.

3. A multi-layer sterilization package according to claim 1 wherein said second layer and said third layer sealed to said unsealed end of said second layer together form a continuous part which corresponds approximately to the dimensions of said first layer.

4. A multi-layer sterilization package according to claim 1 wherein said first and second layers comprise a metallic foil laminated or coextruded with a heat sealable material.

5. A multi-layer sterilization package according to claim 1 wherein said third and fourth layers are approximately coextensive.

6. A multi-layer sterilization package according to claim 1 wherein a body portion defined by said accessible interior space formed between said first and second layers comprises about 50 to 95 percent of the total length of said sterilization package and an operations portion defined by said third and fourth layers comprises about 5 to 50 percent of the total length of said sterilization package.

7. A multi-layer sterilization package according to claim 6 wherein said body portion comprises about 80 to 90 percent of the total length of said sterilization package and said operations portion comprises about 10 to 20 percent of the total length of said sterilization package.

8. A multi-layer sterilization package according to claim 1 wherein all said hermetic seals are continuous and comprise heat seals.

* * * * *